United States Patent [19]

Bunton et al.

[11] 4,106,331
[45] Aug. 15, 1978

[54] METHOD AND APPARATUS FOR DETECTING CONTAMINATION OF LIQUIDS

[75] Inventors: John Darrah Bunton; David John Marsh, both of Bromsgrove, England

[73] Assignee: G.K.N. Group Services Limited, Smethwick, England

[21] Appl. No.: 794,658

[22] Filed: May 6, 1977

[30] Foreign Application Priority Data

May 6, 1976 [GB] United Kingdom ............... 18548/76
Jul. 9, 1976 [GB] United Kingdom ............... 36963/76

[51] Int. Cl.² .................... G01N 25/00; G01N 33/28
[52] U.S. Cl. ............................ 73/61.1 R; 73/15 R; 73/61.3
[58] Field of Search ............... 73/61.1 R, 15 R, 64, 73/61.3, 53

[56] References Cited

U.S. PATENT DOCUMENTS

| | | | |
|---|---|---|---|
| 1,836,316 | 12/1931 | Esau | 73/15 R |
| 2,717,515 | 9/1955 | Pesante | 73/15 R |
| 2,730,894 | 1/1956 | Husa | 73/15 R |
| 2,779,189 | 1/1957 | Corneil | 73/15 R X |
| 2,937,335 | 5/1960 | Toton et al. | 73/15 R X |
| 3,013,427 | 12/1961 | Bender | 73/15 R |
| 3,054,048 | 9/1962 | Bolston et al. | 73/15 R X |
| 3,620,068 | 11/1971 | Cary et al. | 73/15 R |

FOREIGN PATENT DOCUMENTS 2,135,459  12/1972  France ................ 73/15 R

Primary Examiner—Richard C. Queisser
Assistant Examiner—Joseph W. Roskos
Attorney, Agent, or Firm—Spencer & Kaye

[57] ABSTRACT

A method for detecting contamination of a liquid, particularly a Quench Oil, comprises introducing a sensing element at a high temperature into a liquid, allowing the sensing element to commence cooling, and thereafter timing the cooling of the sensing element between two selected temperatures. The time thus measured is compared with a pre-set time, to provide an indication of contamination of the liquid. In apparatus for carrying out the method, a slug of stainless steel in which is embedded a thermo couple is heated in a furnace and then lowered into a receptacle containing the liquid under test. These operations, and the timing and comparison, are effected in a pre-determined automatic cycle.

4 Claims, 4 Drawing Figures

METHOD AND APPARATUS FOR DETECTING CONTAMINATION OF LIQUIDS

BACKGROUND TO THE INVENTION

Field of the invention

This invention relates to a method of, and apparatus for, detecting the presence of contaminants in liquids. The invention has been developed particularly in relation to the detection of contaminants such as water or paraffin in oil which is used in a quenching process for effecting cooling of a work piece, at a controlled rate, from a relatively high temperature by immersion of the work piece in the oil. It will however be appreciated that the invention will find application generally, for example in detection of contamination of lubricating or hydraulic oils.

If oil used for quenching should become contaminated, some extremely disadvantageous and undesirable effects may arise. Firstly, the presence of even a relatively small proportion of water has a great effect, as will hereafter be described in more detail, on the rate and evenness of cooling of a hot work piece immersed therein. This can give rise to the formation of quench cracks in the work piece. In addition to this, quantities of water in quenching oil may, if they come into contact with a hot work piece or if the general temperature in the mass of quenching oil should rise sufficiently high, be vaporised into steam with extreme rapidity which may cause foaming of the oil or even the explosive ejection of oil from the tank or bath in which the operation is taking place. The presence of paraffin in quenching oil is even more undesirable, because of the fire hazard.

Water may be present in quenching oil baths due to condensation effects, or due to leakage of pipes or valves which may, for example, form part of a cooling system for the oil. If there is no agitation of the oil, water would merely remain at the bottom of the tank or bath, but if the oil is subjected to any circulation system (which in practice is very frequently encountered) the water may remain in suspension in the form of droplets in the oil. This effect is aggravated if the oil is washable or contains an emulsifying agent.

It has been proposed hitherto to detect the presence of water in quenching oil by methods involving the abstraction of a sample of the oil, either from a bath or from a circulation system for the oil, and heating of the oil sample to a temperature at which any water therein would vaporise. The vapour pressure of the sample would then rise above that normally to be expected if the oil were pure, and this rise in pressure can then be detected. Such methods, however, have disadvantages in that they tend to be sensitive mainly to the presence of water alone, and are not so sensitive to the presence of other contaminants. Further, problems of adequate or even undue sensitivity can arise with this type of apparatus, and further difficulties with durability of the various components thereof.

SUMMARY OF THE INVENTION

It is an object of the present invention to provide an improved method and apparatus for detecting the presence of contaminants in liquids.

According to one aspect of the present invention, we provide a method of detecting the presence of contaminants in a liquid, comprising introducing a sensing element at a relatively high temperature into a sample of liquid to be tested, allowing the sensing elements to cool to a first temperature, at which the presence of a contaminant in the liquid under test commences to have a suitable effect on the cooling power of the liquid, and measuring the rate at which the sensing element cools from such first temperature to a second, lower, temperature.

The present invention is based upon the discovery that the effect of the presence of a contaminant in an oil does not have a great, or consistent, effect on the initial rate of cooling of a hot article introduced into the oil, the effect on the cooling rate only becoming consistently measurable when the article has cooled to a certain extent from its initial temperature. By not measuring the cooling rate of the sensing means when it is initially introduced into the liquid, the present invention overcomes the introduction of errors which could otherwise occur if such initial cooling rate were measured.

The method preferably provides the measurement of the rate of cooling of the sensing element by measuring the time taken for it to cool from the first to the second temperature, and preferably further comprises the steps of comparing this time with a pre-set time representative of the rate of cooling of the sensing element when in liquid of an acceptable degree of contamination, and furnishing a signal if the measured time does not conform sufficiently closely to the pre-set time.

As applied to the detection of contamination of oils, particularly quenching oils, the method preferably comprises introducing the sensing element into the oil under test at a temperature substantially greater than 500° C (e.g. 800° C), and the time taken for the sensing element to cool is measured between 500° and 200° C.

It has been found that this range is particularly advantageous for measurement. A further fact involved is that, when a quenching oil used for quenching steel is being tested, the range 500° to 200° C is the range in which there is the greatest danger of cracking of a steel article being quenched in the oil, because it is the temperature range in which formation of martensite commences. Thus, the temperature range over which the rate of cooling of the sensing element is measured is that which has most effect on the required physical properties of a work piece undergoing quenching in the oil under test.

According to another aspect of the invention, we provide apparatus for detecting the presence of contaminants in a liquid, such apparatus comprising a sensing element, means for detecting the temperature thereof, means for heating the sensing element to an initial temperature, means for introducing the sensing element when thus heated into a liquid sample to be tested, means for measuring the rate of cooling of the sensing element, and means responsive to the sensing elements attaining a first temperature, at which the presence of contaminants in the liquid under test commences to have a suitable effect on the cooling power of the liquid, for initiating operation of said means for measurement of the cooling rate of the sensing element.

The means for measurement of the rate of cooling of the sensing element may comprise means for measuring the time elapsed between the sensing element's occupying said first temperature and a second predetermined, lower, temperature, and the apparatus may further comprise means for comparing the time thus measured with a pre-set time representative of the rate of cooling of the sensing element when in liquid of an acceptable degree of contamination, and means for furnishing a signal if the measured time does not conform sufficiently closely to the pre-set time.

The sensing element may comprise a slug or billet of a material such as stainless steel, incorporating a thermo couple for detecting the temperature thereof.

The means for heating the sensing element to its initial temperature may comprise a furnace in which the sensing element can be received, disposed immediately above a tank or receptacle in which the sample of liquid under test is held, so that the sensing element may be lowered directly from the furnace into the sample. The furnace may be an electrical resistance furnace or of any other convenient form, and the sensing element may be suspended by a cable or the like for being moved between the furnace and the sample of liquid under test.

BRIEF DESCRIPTION OF THE DRAWINGS

The invention will now be described by way of example with reference to the accompanying drawings, of which.

DESCRIPTION OF THE PREFERRED EMBODIMENT

Figure 1:
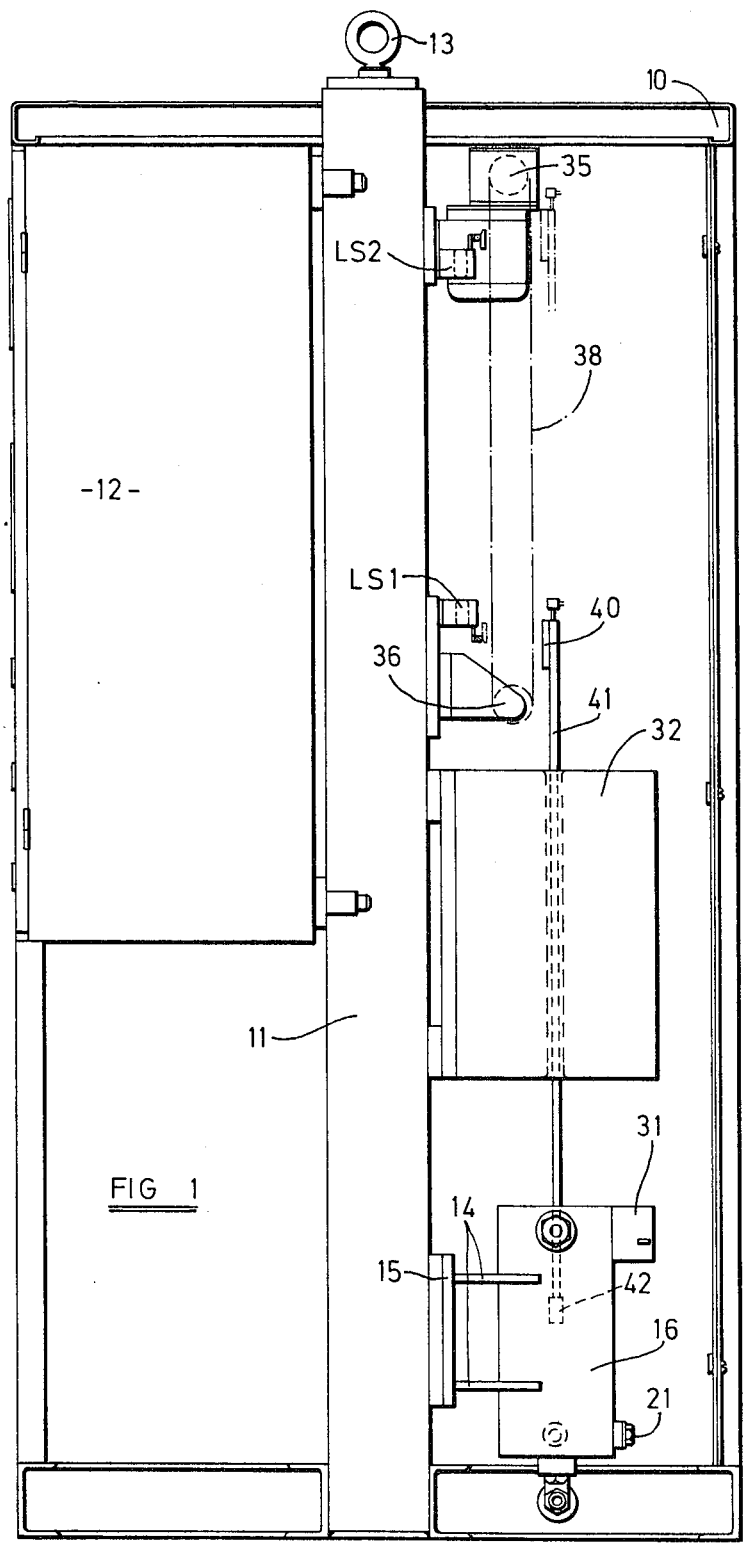
FIG. 1 is a side elevation of apparatus according to the invention.
Figure 2:
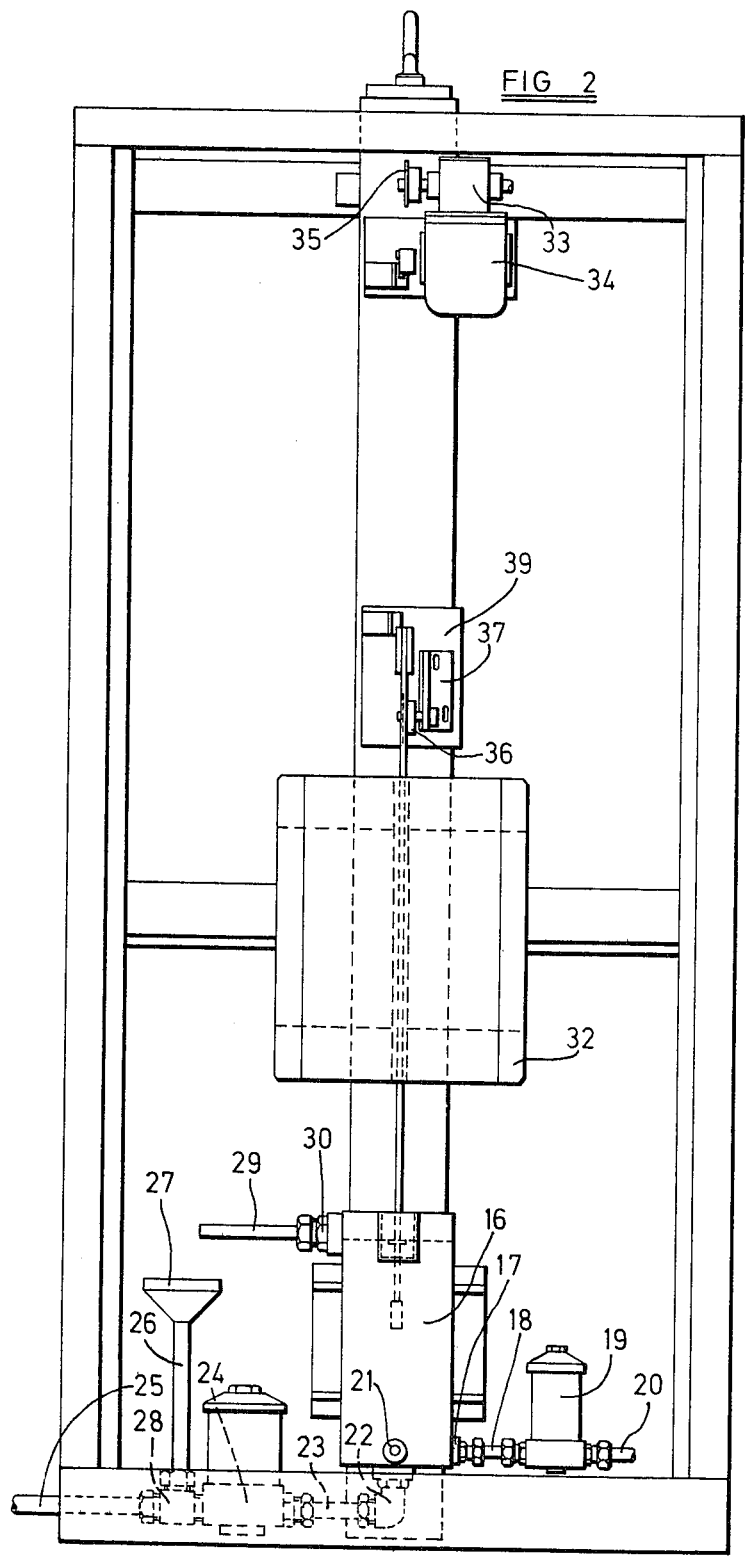
FIG. 2 is a front elevation of the apparatus of FIG. 1.

Referring firstly to FIGS. 1 and 2 of the drawings, the apparatus there illustrated comprises a frame 10 including a central vertical member 11. A box or cabinet 12 for the accommodation of electrical equipment to be described hereafter is located rearwardly of the member 11 within the frame, and the member 11 is provided with a lifting eye 13 for enabling the apparatus to be moved to any desired location.

Towards the lower end of frame member 11 there is mounted, by brackets 14 extending from a plate 15 secured to the member 11, a cup 16 for receiving a sample of liquid, e.g. quenching oil, to be tested. At its lower end, the cup 16 has a connector 17 to which is secured a short length of pipe 18 leading to a solenoid control valve 19. A supply pipe 20 extends from the solenoid control valve 19 to a source, not shown, of liquid to be tested. The cup 16 has a further connector 21 in its side wall, which connector is blanked off but which would be connected to another pipe and solenoid valve arrangement so that liquid from a different source can be introduced into the cup for testing. In its lowermost wall, the cup has a connector and elbow 22 leading to an outlet pipe 23 and solenoid controlled valve 24, the outlet pipe 25 therefrom having a stand pipe 26, with a wide mouth 27, connected thereto by a T-piece 28. An overflow pipe 29 connected by a connector 30 to the cup at the upper part of its side wall terminates above the mouth 27 so that any overflow of liquid from the cup will drain to outlet pipe 25 by way of stand pipe 26.

The cup 16 is also provided with a float-controlled switch, which may be of conventional type, positioned in an extension 31 of the cup. A further float controlled switch, not shown in FIGS. 1 and 2, is positioned at the bottom of the cup 16 for indicating when it is empty.

Vertically above the cup 16, on member 11, there is mounted a furnace 32 which has a vertically extending tunnel for the passage of a probe or sensing element hereafter to be described into and out of the furnace when moved between the furnace and cup 16. The furnace 32 is of the electrical resistance type, but it will be appreciated that other methods of heating the furnace could be utilised.

Above the furnace there is mounted a drive means for effecting movement of the probe or sensing element between the cup 16 and furnace 32, such drive means comprising a geared ⅛ horse-power electric motor 33 mounted on a bracket 34 and having an output sprocket 35, a lower, unpowered, sprocket 36 mounted by a suitable bearing on a bracket 37, and a chain 38 entrained around sprockets 35 and 36. The bracket 37 is vertically adjustable on a mounting plate 39 for tensioning the chain 38. A junction box 40 which supports a temperature resistant electrical cable 41 with sensing element 42 at its lower end is connected to the chain 38, for movement between the positions indicated in solid and broken lines in FIG. 1, which correspond respectively to the sensing element 42 being in the cup 16 and in the furnace 32. Limit switches LS1, LS2 are provided respectively for sensing the raised and lowered positions of the sensing element 42, these limit switches being operated by an operating element, not shown, secured to the adjacent run of chain 38.

Figure 3:
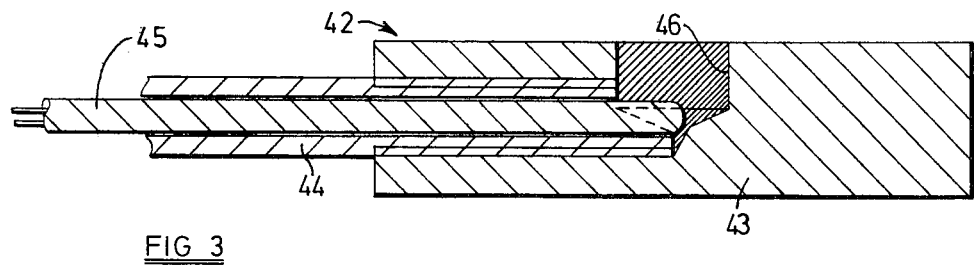
FIG. 3 is a section through a sensing element of the apparatus, on an enlarged scale.

The sensing element 42, shown in greater detail in FIG. 3, comprises a small billet or slug 43 of stainless steel, into a longitudinally extending aperture of which is threadedly secured a stainless steel support tube 44 receiving a "Pyrotenax" mineral insulated thermocouple 45. The thermocouple is welded into the stainless steel slug 43, a side aperture 46 in the slug being filled level to the surface of the slug with weld metal.

Figure 4:
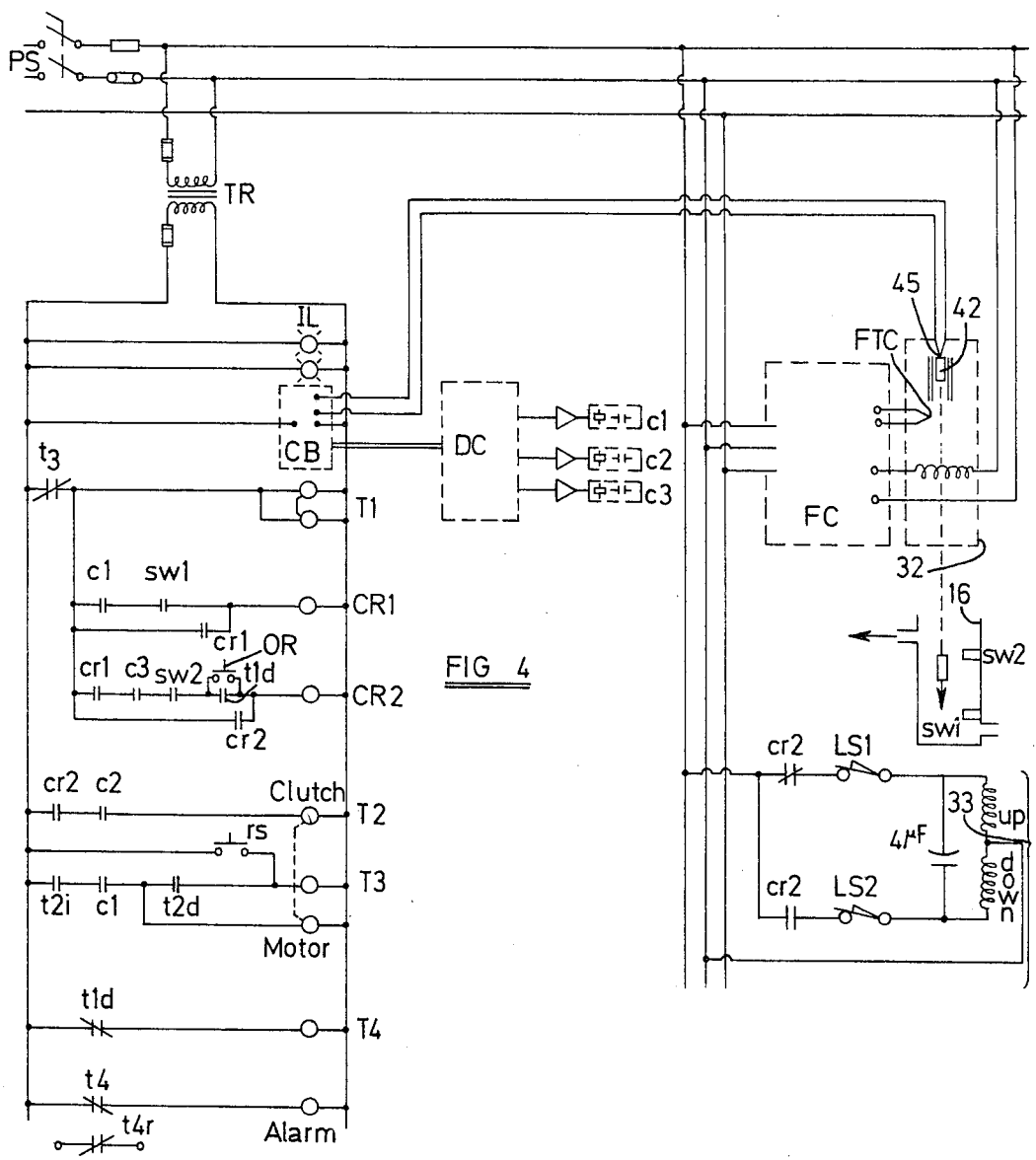
FIG. 4 shows diagrammatically an electrical circuit of the apparatus.

Referring now to FIG. 4 of the drawings, there is illustrated an electrical circuit of the apparatus. This includes a main electrical power supply at PS which supplies a transformer TR as well as a furnace controller FC which controls the power supplied to the heating resistance of furnace 32, the furnace temperature being monitored by a thermocouple FTC. Also fed from the mains power supply is the electric motor 33, which is operable in a sense either to move the sensing element 42 "up" from the test cup to the furnace or "down" from the furnace to the test cup, the motor having "up" and "down" windings energisable respectively through a normally closed contact $cr2$ and limit switch LS1, and a normally open contact $cr2$ and limit switch LS2, the contacts $cr2$ being controlled by a relay CR2 to be described hereafter. Limit switch LS1 opens when the sensing element is fully raised, and limit switch LS2 opens when the sensing element is fully lowered.

The float operated switches in the cup 16, above described, are here designated SW1 and SW2, SW1 being disposed near the bottom of the test cup and having a contact $sw1$ which closes when the liquid level in the test cup falls below this point, and switch SW2 being disposed near the top of the test cup and having a contact $sw2$ which closes when the liquid level within the test cup reaches the switch.

On the secondary side of transformer TR, which supplies a low voltage to the circuits hereafter described, there is connected a control box CB which receives an output from the thermocouple 45 incorporated in the sensing element 42 and provides a binary coded decimal output to a de-coder DC which in turn operates three contacts $c1$, $c2$, $c3$ at respective temperatures. In the particular example under consideration, in which the liquid being tested is quench oil, the de-coder would be set so that contact c1 closes when the sensing element is at a temperature above 200° C, contact c2 closes below 500° C, and contact c3 closes at 620° C plus or minus 2° C.

Also connected to the secondary of transformer TR are indicator lamps IL to indicate when the supply is "on", and the following components:

T1, a delay timer (0 to 60 minutes), having normally closed and normally open contacts t1d, T2, a delay timer (0 to 30 seconds), having normally open instantaneous and delayed operation contacts t2i, t2d, T3, a delayed drop-off relay giving a 0.25 seconds delay, having a normally closed contact t3, T4, a delayed drop-off relay (adjustable up to one minute) having normally closed contacts t4, CR1 a relay which controls the solenoid valve 19, 24 controlling flow of liquid into and out of the test cup 16, CR2, a relay which controls the drive motor by way of contacts cr2 as described above.

The normally closed contact t4 of relay T4 is connected in series with an alarm, and a further such contact t4r may operate a remote alarm.

The operation of the apparatus will now be described, and it is believed that other features of the electrical circuit thereof will become apparent. Initially, when the mains electrical power supply is switched on, the following occurs:

i. Relay T4 is energised via the normally closed contact t1d of timer T1, thereby opening the normally closed t4 contact in series with the alarm.

ii. Power is applied to the resistance winding of the furnace 32, via the furnace controller FC.

iii. The drive motor 33 raises the sensing element 42 into the furnace (if it is not already there), via the normally closed contact cr2, such movement being terminated by the opening of limit switch LS1.

iv. Timer T1 starts to time.

If the test cup 16 is empty (as detected by float switch SW1), then when the temperature of the sensing element exceeds 200° C relay CR1 is energised by way of contact c1. This opens the inlet solenoid valve 19 and closes the drain solenoid valve 24. The test cup 16 then fills, and operates the float switch SW2. When, in addition to this, the sensing element achieves 620° C (therefore closing contact c3) and the delayed contact t1d on the time T1 operates, relay CR2 is energised and latches, causing the drive motor 33 to lower the sensing element into the test cup. As the temperature of the sensing element falls below 500° C, the clutch of timer T2 energises by way of contact c2, and its motor is energised via the instantaneous contact t2i of timer T2 and contact c1 which is closed while the temperature of the sensing element exceeds 200°. T2 therefore commences to time. Two possible sequences of operation are now possible:

i. If the time set on timer T2 expires before the temperature of the sensing element has fallen below 200° C, then timer T3 is energised via the delayed contacts t2d of timer T2. This re-sets timer T1, and relays CR1 and CR2, which in turn re-sets timers T1 and T3. This then raises the sensing element back into the furnace and causes the cup 16 to drain.

The delayed drop-off relay T4 is set for a slightly longer time than that which is required for the above cycle of operation to be completed. Hence its normally closed contact t4 should not have released before timer T1 is re-set, and the alarm circuit is not activated.

ii. If the sensing element has cooled below 200° C before the timer T2 has timed out, T3 is not energised and none of the timers or relays is re-set. T4 will thus expire, and its contact in series with the alarm will open, activating the alarm. Timer T2 will retain the reading of the time which has taken for the cooling of the sensing element between 500° C and 200° C, and the sensing element will remain in the cup.

It will be noted that if the test sequence should be delayed by the failure of any component other than timer T1, timer T4 will expire and the alarm will be operated. It would then be necessary for an operator to investigate why the test sequence has not been completed in the allotted time.

A manually operated contact rs is connected in parallel with the sets of contacts t2i, c1, and t2d which operate relay T3, for re-setting the alarm.

If the alarm has not been operated, and T1 has therefore been re-set, the test sequence will be repeated, the time to which T1 is set determining the frequency of such repetition. A manually operable override switch OR is provided if the test is desired to be repeated before the time set on T1 has expired.

The alarm may be audible and/or visible, and could even be arranged automatically to shut down plant or apparatus using the liquid under test if the test shows an undesirable degree of contamination to be present.

It will of course be appreciated that the temperatures which are selected for the various measurements can be varied to suit the particular liquid which is being tested, or contaminant which is being detected. The temperatures given above are those applicable to the application for which the invention has been developed, namely the testing of quench oils, and the results of some such tests are given hereafter.

| | TIME IN SECONDS 500 – 200° C | | |
|---|---|---|---|
| OIL | With 0.1% water | With 5% paraffin | Normal |
| FENSO 40 (slow quench oil) | 8.6 | 15.1 | 24.8 |
| FENSO 41 (med. quench oil) | 9.9 | 17.5 | 24.6 |
| FENSO 36 (fast quench oil) | 6.1 | 7.0 | 7.1 |
| FENSO 70 (marquench oil | 13.2 | 16.2 | 18.9 |
| Transformer oil | 9.0 | 15.4 | 22.4 |
| Hydraulic oil | 10.1 | 20.3 | 28.2 |

| | TIME IN SECONDS 800 – 500° C | | |
|---|---|---|---|
| Oil | With 0.1% water | With 5% paraffin | Normal |
| FENSO 40 (slow quench oil) | 3.6 | 5.4 | 6.0 |
| FENSO 41 (med. quench oil) | 2.6 | 3.2 | 2.9 |
| FENSO 36 (fast quench oil) | 3.1 | 3.3 | 2.8 |
| FENSO 70 (marquench oil) Transformer | 4.5 | 5.3 | 4.8 |

| Oil | TIME IN SECONDS 800 - 500° C | | |
|---|---|---|---|
| | With 0.1% water | With 5% paraffin | Normal |
| oil | 5.6 | 7.0 | 4.6 |
| Hydraulic oil | 3.0 | 5.2 | 3.7 |

It will be noted from these tables that the effect of either water or paraffin on all the oils tested is to increase the rate at which cooling of the probe between the temperatures of 500° and 200° C takes place. In the "FENSO 36" fast quenching oil, the effect on the actual cooling time of the probe is not as great as it is for the slower quenching oils, but it still represents a measurable distinction between pure and contaminated oil. In the case of cooling of the probe from 800° to 500° C, however, the effect of the different contamination some of the oils is to speed up cooling, whilst in other oils cooling is slowed. For example, 5% paraffin in "FENSO 41" oil slows the rate of cooling from 800° to 500° C but 0.1% water speeds cooling between these temperatures. Compared with this, the effect on "FENSO 40" oil of water contamination is the same as that of paraffin contamination, namely to increase the rate of cooling of the probe between 800° and 500° C.

Thus, permitting the probe to cool to a temperature of approximately 500° C before measuring its cooling rate enables accurate and consistent measurement, of possible contamination of the oil, to be achieved. In general, suitable selection of the temperature range over which the cooling is measured can enable the detection of quantities of water as low as 0.02%.

In various modifications of the method and apparatus, the cup which contains the liquid under test may be included in a circulation system for such liquid, so that the probe is in fact introduced into flowing liquid rather than stationary. This could reduce or eliminate any buildup of contaminants which could occur in the test cup.

We claim:

1. A method of detecting fluid contaminants in a liquid comprising the steps of
heating a temperature sensing element to a relatively high initial temperature;
immersing said sensing element in a sample of the liquid to be tested;
allowing said sensing element to cool naturally in said liquid until a first predetermined temperature below said initial temperature is reached;
initiating timing means in response to the element reaching said first predetermined temperature;
allowing said sensing element to continue cooling naturally in said liquid until a second predetermined temperature is reached;
measuring the time interval between the initiation of the timing means and the sensing element reaching said second predetermined temperature;
and comparing said time interval with a time interval representing the rate of cooling of the sensing element in a sample of the liquid having an acceptable level of contamination, between the same first and second predetermined temperatures, said first and second predetermined temperatures being selected, in accordance with the type of liquid to be tested, as delimiting a range of temperatures over which the presence of fluid contaminants in the liquid causes a substantial measurable deviation from the normal cooling power of the liquid.

2. A method of detecting fluid contaminants in quench oil comprising the steps of:
heating a temperature sensing element to a relatively high initial temperature substantially greater than 500° C.;
immersing said sensing element in a sample of the quench oil to be tested;
allowing said sensing element to cool naturally in said liquid until a temperature of 500° C. is reached;
initiating timing means in response to the element reaching 500° C.;
allowing said sensing element to continue cooling naturally in said liquid until a temperature of 200° C. is reached;
measuring the time interval taken by the sensing element to cool in the quench oil from 500° C. to 200° C. and comparing said time interval with a known time interval taken by a sample of quench oil having an acceptable level of contamination to cool the sensing element through the same range of temperatures.

3. Apparatus for detecting the presence of fluid contaminants in a liquid, such apparatus comprising a temperature sensing element, means for detecting the temperature thereof, means for heating the sensing element to a relatively high initial temperature, means for introducing the temperature sensing element when thus heated into a liquid sample to be tested, measuring means for measuring the rate of cooling of the sensing element, and initiation means initiating operation of said measuring means when the sensing element is immersed in the liquid and attains a first predetermined temperature below said initial temperature, the measuring means then measuring the time which elapses between the sensing element having said first predetermined temperature and having a second predetermined, lower, temperature, said first and second predetermined temperatures being selected, in accordance with the type of liquid to be tested, as delimiting a range of temperatures over which the presence of fluid contaminants in the liquid causes a substantial measurable deviation from the normal cooling power of the liquid.

4. Apparatus for detecting the presence of fluid contaminants in a quench oil, the apparatus comprising a temperature sensing element, means for detecting the temperature thereof, means for heating the sensing element to a temperature substantially greater than 500° C., means for introducing the sensing element when thus heated into a sample of quench oil to be tested, measuring means for measuring the rate of cooling of the sensing element and initiation means initiating operation of the measuring means when the sensing element is immersed in the quench oil and attains therein a temperature of 500° C., the measuring means then measuring the time which elapses between the sensing element having a temperature of 500° C. and cooling to a temperature of 200° C.

* * * * *